United States Patent [19]
Grumet

[11] Patent Number: 5,532,275
[45] Date of Patent: Jul. 2, 1996

[54] METHOD OF PROMOTING WOUND HEALING AND SCAR REGRESSION

[75] Inventor: Martin Grumet, New York, N.Y.

[73] Assignee: Andrx Pharmaceuticals, Inc., Fort Lauderdale, Fla.

[21] Appl. No.: 351,778

[22] Filed: Dec. 7, 1994

[51] Int. Cl.$^6$ .................................................. A61K 31/195
[52] U.S. Cl. .................................. 514/567; 424/DIG. 13
[58] Field of Search ..................... 514/67, 567; 424/60, 424/DIG. 13

[56] References Cited

U.S. PATENT DOCUMENTS 4,154,823  5/1979  Schutt .................................. 424/195.1

*Primary Examiner*—John W. Rollins
*Attorney, Agent, or Firm*—Hedman, Gibson & Costigan

[57] ABSTRACT

A novel method of treating wounds has been discovered that is based on the system and/or topically administration of an effective amount, of para-amino benzoic acid or its derivatives, to a patient who has a wound, the healing of the wound will be promoted and scar formation will be reduced. In addition, it has been discovered that by systemically and/or topically administering an effective amount of para-amino benzoic acid or its derivatives, to a patient who has scar tissue or keloids, the scar tissue and/or keloid tissue will regress and/or soften to allow the skin in the area of the scar or keloid to become more flexible.

4 Claims, No Drawings

METHOD OF PROMOTING WOUND HEALING AND SCAR REGRESSION

BACKGROUND OF THE INVENTION

1. Field of the Invention

This invention relates to a method of treating wounds, which are caused by trauma or by surgical procedures, to promote healing and reduce scarring. In addition the invention also provides a method for softening and/or reducing the severity of pre-existing scars and keloids.

2. Description of the Related Art

In the prior art, wound treatment has been based on restoring the integrity of skin by use of sutures, staples or various adhesive closures. Systemic and local anti-infectives have been used to treat and prevent infections which are caused by microscopic flora. To promote wound healing, topical preparations of oil soluble vitamins such and Vitamin A, D and E have been applied to healing wounds but the efficacy of these treatments has not been established by controlled clinical studies. Para-amino benzoic acid has been used in the treatment of Peyronie's disease and in the treatment of scleroderma where it has anti-fibrotic activity.

SUMMARY OF THE INVENTION

It has been discovered that by systemically and/or topically administering an effective amount, of para-amino benzoic acid or its derivatives, to a patient who has a wound, the healing of the wound will be promoted and scar formation will be reduced. In addition, it has been discovered that by systemically and/or topically administering an effective amount of para-amino benzoic acid or its derivatives, to a patient who has scar tissue or keloids, the scar tissue and/or keloid tissue will regress and/or soften to allow the skin in the area of the scar or keloid to become more flexible.

Accordingly, it is a primary object of this invention to provide a method for promoting the healing of wounds.

It is also a primary object of this invention to provide a method of promoting the healing of wounds with a reduction of the formation of scar tissue.

It is also a primary object of this invention to provide a method of inducing the regression of scar tissue.

It is also a primary object of this invention to provide a method of inducing the regression of keloid tissue.

These and other objects of the invention will become apparent from a review of the specification.

DETAILED DESCRIPTION OF THE INVENTION

The present invention provides a method of treating wounds which comprises administering an effective amount of a compound of Formula I:

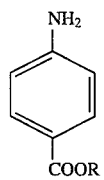

(I)

where R is selected from the group consisting of hydrogen sodium and potassium to a patient who has a wound, said compound being administered in an amount which is sufficient to promote the healing of a wound.

The method comprises the oral administration of a compound of Formula I to a patient who has a wound as a result of trauma or surgery at a dose of 100 mg/kg to 200 mg/kg per day in divided doses. The administration of the compound of Formula I should begin as soon as practicable after the wound is inflicted and may be continued until the healing process produces stable tissue. Generally, treatment With surgical patients, pre-operative administration of the compound may be utilized to maximize the benefits of the invention. This period of time may be from 2 to 12 weeks. Depending upon the response of the patient, the dose and period of treatment may be varied.

When the compound of Formula I is used to cause regression of scars, treatment may be initiated at any time without regard to the age of the scar. The treatment is of benefit for old scars in that it will cause some regression and will soften the scar tissue and will cause the skin to become more pliant and flexible. This can be of significant benefit when scar tissue inhibits the free movement of a joint. In addition the invention also provides a method for inhibiting the formation of and/or softening and/or reducing the severity of keloids. When scars and/or keloids are treated prophylacticly, for regression, or by surgical excission, the same dose and treatment schedule may be used that is employed when the compound of Formula I is used for the treatment of wounds.

The invention also includes the topical application of a compound of Formula I for the same purposes that oral administration is employed. Generally a petrolatum base ointment or a water washable base may be utilized for topical administration which has a concentration of from 0.5 wt % to 5 wt % of a compound of Formula I.

EXAMPLE 1

Para-amino benzoic acid is formulated into an ointment having the following composition:

| | |
|---|---|
| Propylene glycol | 10.0 g |
| White petrolatum | 940.0 g |
| Lanolin anhydrous | 30.0 g |
| Para-amino benzoic acid | 10.0 g |

EXAMPLE 2

Para-amino benzoic acid is formulated into an ointment having the following composition:

| | |
|---|---|
| Propylene glycol | 10.0 g |
| Sodium lauryl sulfate | 10.0 g |
| White petrolatum | 250.0 g |
| Stearyl alcohol | 250.0 g |
| Polysorbate 80 | 8.0 g |
| Methylparaben | 0.25 g |
| Propylparaben | 0.15 g |
| Purified Water | 370.0 g |
| Para-amino benzoic acid | 10.0 g |

EXAMPLE 3

Patient A (male, age 64) had hypertrophic scars on his back and wrist which resulted from injuries and had been present for a period of more than ten years prior to treatment. The patient developed Peyronnies disease approximately two years prior to treatment with 12.0 g/day of para-amino benzoic acid which was administered orally in three divided doses. After 12 weeks, the patients scars showed a marked reduction in thickness and hardness. Treatment continued for more than one year with progressive softening and regression of the scars.

EXAMPLE 4

Patient B (male. age 35) underwent surgery on the hand for reconstruction of the second joint on the middle finger. The surgery required a 5 cm. incision which was closed with sutures. Six months later, the patient was treated with 12.0 g/day of para-amino benzoic acid which was given orally in three divided doses. After two months of therapy, it was apparent that the scar tissue had been reduced and that the adjacent joint showed dramatically increased flexibility.

EXAMPLE 5

Patient C (female, age 27) who had a keloid (8×6 mm) on the mid-back, was treated with the preparation of Example 1. After 7 weeks the size of the keloid was reduced (7×6 mm) and the keloid was softer and flatter.

EXAMPLE 6

Patient D (male, age 35) who had a large firm keloid on the mid-chest was treated twice daily by covering the surface with a thin film of the preparation of Example 2. After one month the lesion was softer and flatter than when treatment began.

I claim:

1. A method of treating wounds which comprises orally administering an effective amount of a compound of Formula I:

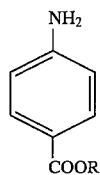

where R is selected from the group consisting of hydrogen sodium and potassium to a patient who has a wound, said compound being administered in an amount which is sufficient to promote the healing of a wound.

2. A method as defined in claim 1 wherein the compound of Formula I is para-aminobenzoic acid.

3. A method as defined in claim 1 wherein the compound of Formula I is para-aminobenzoate, sodium salt.

4. A method of treating scar tissue to cause said scar tissue to regress said treatment comprising the oral administration of a compound of Formula I:

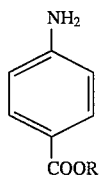

where R is selected from the group consisting of hydrogen sodium and potassium to a patient who has scar tissue, said compound being administered in an amount which is sufficient to promote the regression of scar tissue.

* * * * *